US006893410B1

(12) United States Patent
Hely

(10) Patent No.: US 6,893,410 B1
(45) Date of Patent: May 17, 2005

(54) MULTI-ADJUSTABLE WRIST BRACE

(75) Inventor: John P. Hely, Oxnard, CA (US)

(73) Assignee: Weber Orthopedic Inc., Santa Paula, CA (US)

( * ) Notice: Subject to any disclaimer, the term of this patent is extended or adjusted under 35 U.S.C. 154(b) by 53 days.

(21) Appl. No.: 10/310,453

(22) Filed: Dec. 4, 2002

(51) Int. Cl.[7] ............................................. A61F 13/00
(52) U.S. Cl. ......................................... 602/21; 602/64
(58) Field of Search ............................. 602/64, 20, 21, 602/5; 128/877, 878

(56) References Cited

U.S. PATENT DOCUMENTS

| 1,471,948 | A | * | 10/1923 | Cox et al. ..................... 602/22 |
| 2,206,404 | A | | 7/1940 | Jones |
| 4,854,309 | A | | 8/1989 | Elsey |
| 5,014,689 | A | * | 5/1991 | Meunchen et al. ........... 602/21 |
| 5,160,314 | A | * | 11/1992 | Peters ........................... 602/21 |
| 5,415,624 | A | * | 5/1995 | Williams ....................... 602/21 |
| 5,769,804 | A | | 6/1998 | Harris et al. |
| 5,982,285 | A | | 11/1999 | Buche et al. |
| 6,024,715 | A | | 2/2000 | Maxwell |
| 6,398,748 | B1 | | 6/2002 | Wilson |
| D477,409 | S | * | 7/2003 | Mills et al. ................ D24/190 |

* cited by examiner

Primary Examiner—Henry Bennett
Assistant Examiner—Kathryn Odland
(74) Attorney, Agent, or Firm—William W. Haefliger

(57) ABSTRACT

A wrist brace, comprising a flexible holder to receive the user's wrist and having two flaps adapted to be closed toward one another to secure the holder about the wrist; tightening strands associated with the flaps; a puller connected with all the strands to be pulled to tension the strands as the flaps are moved toward one another, the puller then being adjustably connectible to the holder to adjustably tension all of the strands. A flexible auxiliary strap may be connected to the holder to be adjustably folded over a zone between the user's thumb and forefinger, for adjustable connection to the holder, for firmly anchoring the holder in position on the wrist. The strands may be anchored to an over-flap to be adjustably positioned relative to the puller.

18 Claims, 3 Drawing Sheets

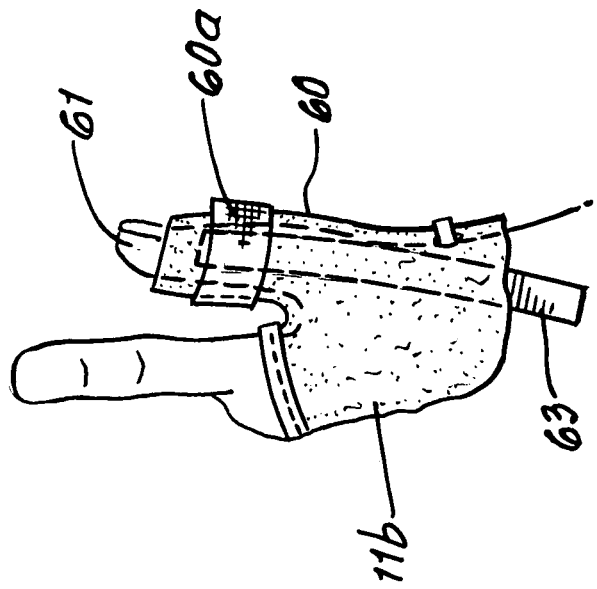
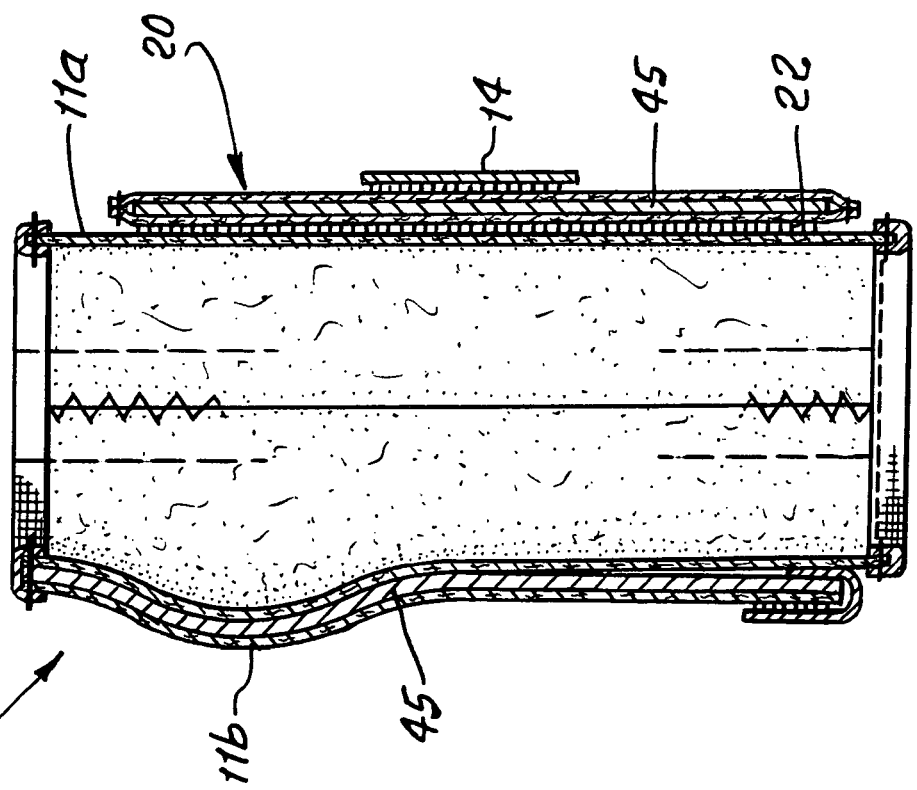

MULTI-ADJUSTABLE WRIST BRACE

BACKGROUND OF THE INVENTION

This invention relates generally to wrist braces, and more particularly to improvements in braces enabling ease and readiness of attachment and tightening about the wrist of the wearer, as well as closeness of fit to different sizes of wrists, and retention between the thumb and forefinger of the user.

Prior wrist braces lacked the unusually advantageous combinations of features referred to, as well as the wide ranges of fit and adjustability both about the wrist, and also over the zone between the thumb and forefinger. There is need for the multiple improvements in a wrist brace as is now afforded by the invention.

SUMMARY OF THE INVENTION

It is a major object of the invention to provide a wrist brace construction and configuration meeting the above need. Basically, the improved wrist brace comprises:

a) a flexible holder to receive the user's wrist and having two flaps adapted to be closed toward one another to secure the holder about the wrist, b) tightening strands associated with the flaps, and having anchored ends bodily adjustable relative to at least one of said flaps, c) a puller connected with all the strands to be pulled to tension the strands as the flaps are moved toward one another, the puller then being adjustably connectible to the holder to adjustably tension all of the pulled strands, d) and a flexible auxiliary strap connected to the holder to be adjustably folded over a zone between the user's thumb and forefinger, for adjustable connection to the holder, for firmly anchoring the holder in position on the wrist.

It is another object to provide an improved wrist brace as referred to wherein the puller and holder carry connective material, which typically includes hook and pile components, the connective material carried by the holder being distributed over an area which is much greater than the area of the connective material on the puller.

Yet another object is to provide a wrist brace in which the flexible auxiliary strap also carries connective material which adjustably attaches to the connective material on the holder.

An additional object is to provide for adjustable anchoring of the strands to the second of the two flaps in spaced relation to the auxiliary strap.

Additional objects include provision of between 4 and 6 strands merging toward and connected to the one puller which itself has the form of a flexible strap; the provision of a holder which has flexible U-shaped cross section; and the provision of of strand passage through one of the two flaps, the other of the two flaps including a main flap, there being an over-flap detachably and adjustably carried by the main flap, the strands having anchored connection to that over flap, to adjustably position and anchor the strand ends relative to said other flap. Also, the puller is configured to be adjustably attached to the over flap, whereby multiple adjustments maximize comfort and bracing effect.

These and other objects and advantages of the invention, as well as the details of an illustrative embodiment, will be more fully understood from the following specification and drawings, in which:

DRAWING DESCRIPTION

FIG. 5 is an enlarged section taken on lines 5—5 of FIG. 1; and

FIG. 6 is a fragmentary view showing a thumb brace.

DETAILED DESCRIPTION

Figure 2:
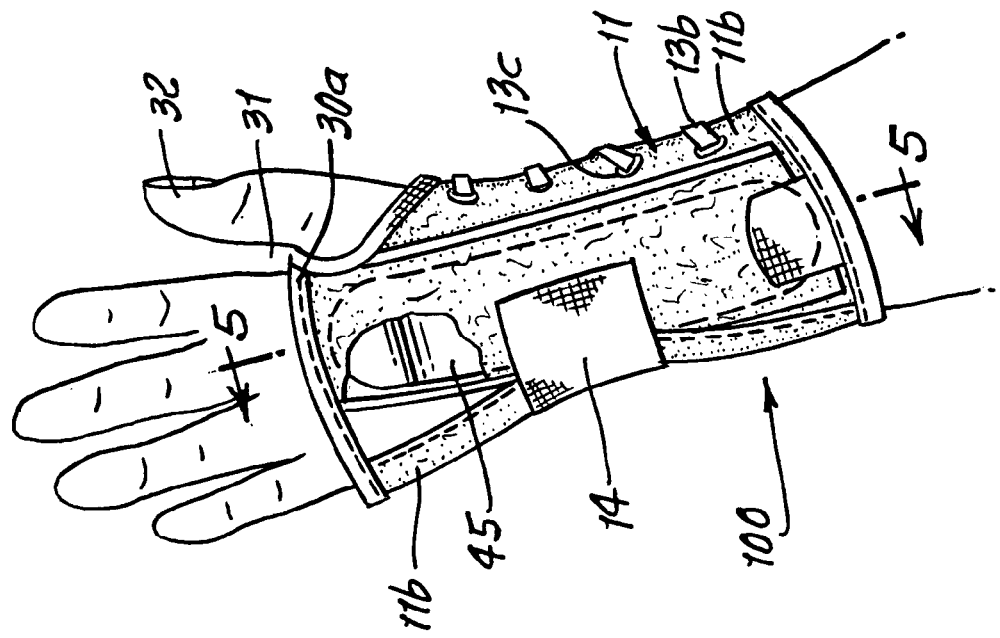
FIG. 2 is a perspective view of the opposite side of the FIG. 1 apparatus, when connected to a wrist.

In the drawings, the preferred brace 100 includes an elongated flexible holder, in the form of a sleeve 11, is sized to loosely receive the user's or wearer's wrist 12. The sleeve includes two flexible flaps, first flap 11a and second flap 11b, adapted to be relatively closed toward sides of the wrist to secure the holder sleeve about the wrist.

Tightening or tensioning strands 13 are associated with the flaps. They are effectively anchored at end locations 13a to the flap 11a when the holder is secured about the wrist, and then extend at 13b between the flaps and through openings 13c in flap 11b. The strands then extend at 13d, and convergently in FIG. 1, toward a tightener flap 14 to which the strands are end connected at locations 13e, in merged condition. Flap 14 may be elongated, as in FIGS. 1 and 2. The locations 13a are spaced apart at substantially equal intervals lengthwise of the flap 11a and sleeve; openings 13c are likewise spaced apart at substantially equal intervals along flap 11b the same as the intervals between locations 13a. Accordingly, only one tightener 14 is required to be hand manipulated, by pulling force, for adjustably tightening all of the strands as the flaps 11a and 11b are moved toward one another, and fastened. Also, angular movement of the tightener flap, in direction 101 or direction 102, i.e. lengthwise of the sleeve, during such pulling, achieves lesser or greater tightening of different strands, for adjusting the securing of the holder to the wrist configuration of the user, for maximum comfort consistent with optimum security, and bracing effect. Spaced apart stiffening inserts (to be more fully described) in the sleeve, as at 45 in strand anchoring over-flap 20, can be employed to assist in such bracing; however, they are also subject to the referenced adjustment of different portions of the holder to the wrist configuration, to assist in obtaining the optimum adjusted bracing or immobilizing effect, consistent with comfort. This obviates any need for a rigid or semi-rigid sleeve, which would not be nearly as conformable to the wrist configuration.

Figure 1:
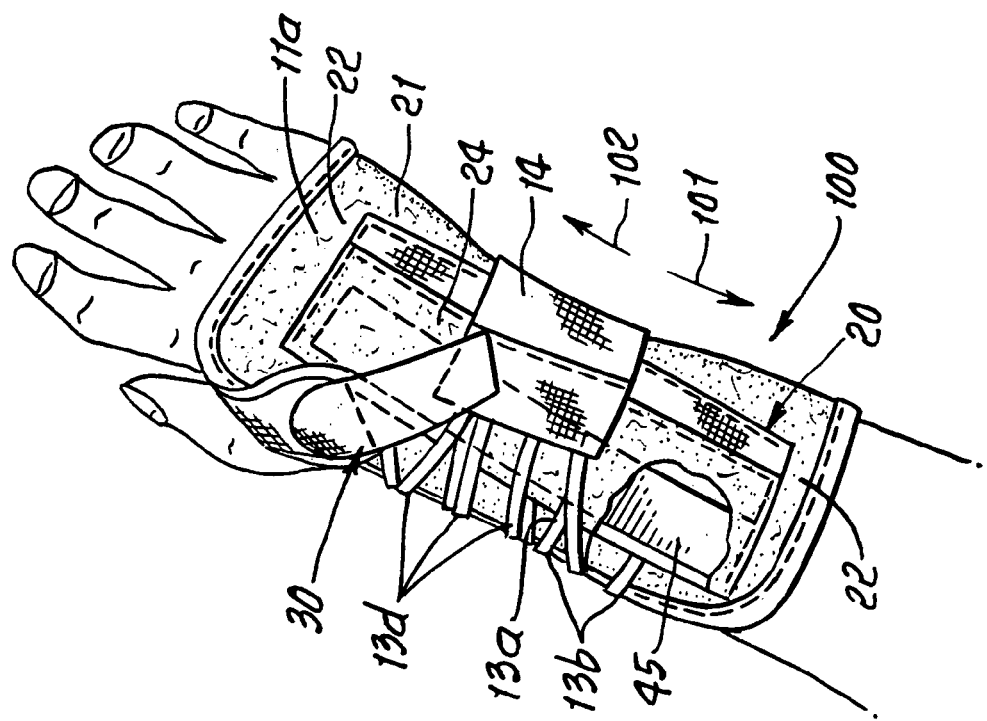
FIG. 1 is a perspective view of one side of apparatus incorporating the invention when connected to a wrist.
Figure 3:
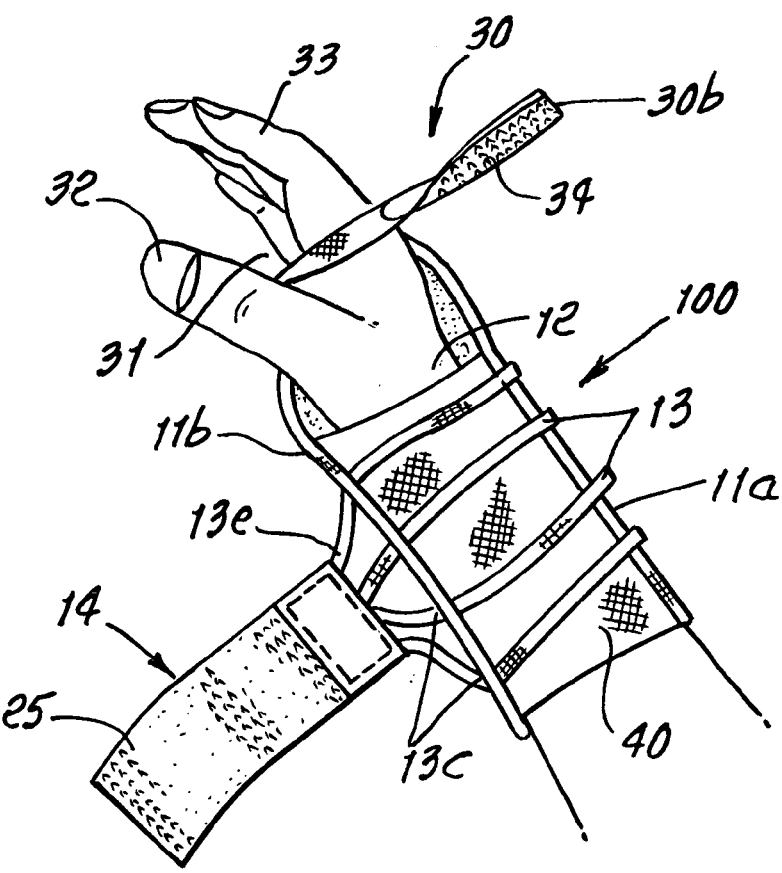
FIG. 3 is a side view of the FIG. 1 and FIG. 2 apparatus during a stage of application to a wrist, the apparatus elements being positioned for tightening and interconnection.

It is a feature of the invention that the carriage of the strands at end locations 13a is made to be adjustable, whereby all of those end locations are simultaneously adjustable in position, and all of the opposite end locations 13e of the strands are simultaneously adjustable in position by the tightener 14 relative to adjusted end locations 13a, affording a very high degree of adjustability. Adjustment of both ends of the strands is thereby achieved. For this purpose, the strands at end locations 13a are preferably anchored in position to an over flap 20, or sub-flap, which is adjustably attached or attachable (face to face) to a main flap 21. The latter functions as a part of flap 11a when the brace is attached to the wrist. As shown in FIG. 1 the tightener flap 14 is attachable to and over the over flap 20, to assist in its attachment to the main flap 21, a local part of flap 11a, providing a self-restraining, unitary, layered assembly of elements, held in adjusted relative positions for comfort, security and maximum bracing effect.

Figure 4:
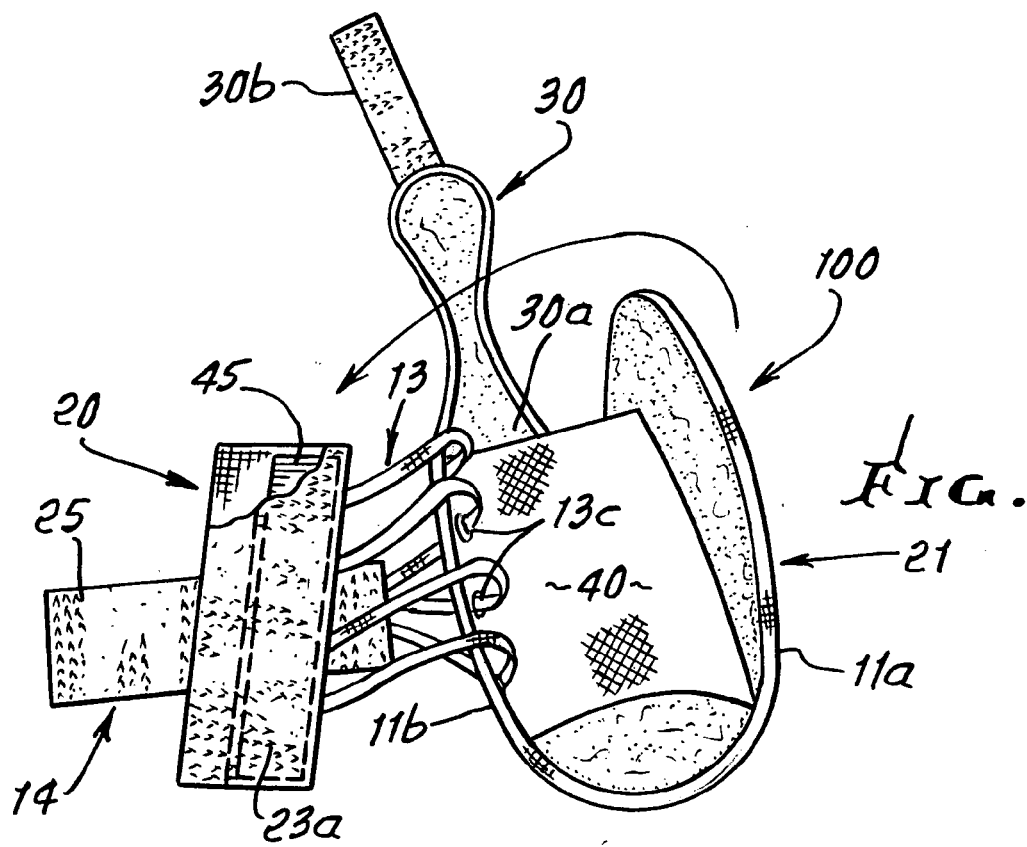
FIG. 4 is a view of the holder apparatus with its elements in distended positions, prior to wrist insertion.

The elements which are retained together in face to face relation may employ connective, or hook and pile material, as follows:

- wide area connective material 22 on flap 11a (for example extending along 11a and near opposite ends of 11a)
- a band 23a of connective material (see FIG. 4) on the inner side of over-flap 20, to press connect to material 22 in different positions of 20 (see FIG. 1)
- a band 24 of connective material on the opposite (outer) side of over-flap (see FIG. 1)
- a band 25 of connective material on the inner side of puller flap 14 (see FIG. 4), to press connect to selected part or parts of band 24 (note elongation of band 24 and of the over-flap, to provide for or enable such selected postion adjustment.

Also provided, if required, is a flexible auxiliary strap connected to the holder to be adjustably folded over a zone between the user's thumb and forefinger, for adjustable connection to the holder, for firmly anchoring the holder in position on the wrist. See strap 30, having an end portion 30a attached to flap 11b, and elongated to extend over zone 31 between the thumb 32 and forefinger 33 of the wearer. Strap 30 has an end portion 30b carrying connective (hook or pile) material 34 that is adjustably press-attachable to the material 22 on flap 11a, and/or to exposed material 24 on the over flap 20.

If desired, plastic or metallic stiffeners may be provided in the elongated flexible material of the over flap 20 as referred to above. See broken lines 45.

Also shown is a flexible web 40 that interconnects the two flaps 11a and 11b, to hold them in spread apart, U-shaped connection, for insertion of the user's wrist, at the time of brace fitting to the wrist. Web 40 is typically spaced downwardly within the U-shaped configuration of the flaps 11a and 11b.

FIG. 6 shows a flexible flap extension 60 receiving the user's thumb 61. Extension 60 is shown as integral with flap 11b, and may include a wrap-around VELCRO connected strap 60a. An elongated metallic stiffener 63 is associated with flap 11b. A stiffener extension 63a extends at the flap extension 60 to brace the thumb 61. Extension 63 may be received in a pocket in the flap material.

I claim:

1. A wrist brace, comprising in combination
   a) a flexible holder to receive the user's wrist and having first and second flaps adapted to be closed toward one another to secure the holder about the wrist,
   b) tightening strands associated with said flaps, and having anchored ends bodily adjustable relative to at least one of said first and second flaps,
   c) a tightener connected with all the strands to be pulled to tension the strands as the first and second flaps are moved toward one another, the tightener then being adjustably connectible to the holder to adjustably tension all of the strands,
   d) and a flexible auxiliary strap connected to the holder to be adjustably folded over a zone between the user's thumb and forefinger, for adjustable connection to the holder, for firmly anchoring the holder in position on the wrist,
   e) the first flap of the two flaps including a main flap, and there being an over flap carried by the main flap, said strands anchored to said over flap to adjustably position strand ends relative to said second flap.

2. The combination of claim 1 wherein there are openings through the first flap to pass the strands, the openings spaced apart in a row proximate an edge of said first flap.

3. The combination of claim 2 wherein all the strands after passing through said openings extend openly toward one another and then convergently toward an end portion of the tightener, the strands being spaced apart at substantially equal intervals, at said openings.

4. The combination of claim 1 wherein the tightener and holder carry connective material which includes hook and pile components, the connective material carried by the holder being distributed over an area which is much greater than the area of the connective material on the tightener.

5. The combination of claim 4 wherein the tightener has the form of a flexible strap.

6. The combination of claim 5 wherein the auxiliary strap also carries connective material which attaches to said connective material on the holder.

7. The combination of claim 2 wherein the strands have adjustably anchored connection to the second flap, in spaced relation to the auxiliary strap when said auxiliary strap is adjustably connected to said connective material on the holder.

8. The combination of claim 1 wherein the flexible holder has U-shape cross-section.

9. The combination of claim 8 wherein the strands extend through the first flap, and are simultaneously effectively adjustably anchored to the second flap.

10. The combination of claim 9 wherein there are between 4 and 6 of said strands, which openly merge toward said tightener.

11. A wrist brace, comprising in combination
   a) a flexible holder to receive the user's wrist and having first and second flaps adapted to be closed toward one another to secure the holder about the wrist,
   b) tightening strands associated with said flaps, and having anchored ends bodily adjustable relative to at least one of said first and second flaps,
   c) a tightener connected with all the strands to be pulled to tension the strands as the first and second flaps are moved toward one another, the tightener then being adjustably connectible to the holder to adjustably tension all of the strands,
   d) and a flexible auxiliary strap connected to the holder to be adjustably folded over a zone between the user's thumb and forefinger, for adjustable connection to the holder, for firmly anchoring the holder in position on the wrist,
   e) the strands extending through one of said first and second flaps, and being simultaneonsly adjustable anchored to the other of said first and second flaps,
   f) and wherein said first flap includes a main flap, there being an over flap detachably and adjustably carried by the main flap, said strands anchored to said over flap, to adjustably position strand ends relative to said second flap.

12. The combination of claim 11 wherein said over flap and main flap have hook and pile interconnection.

13. The combination of claim 11 wherein the tightener is adjustably attached to the over flap.

14. A wrist brace, comprising in combination
   a) a flexible holder to receive the user's wrist and having first and second flaps adapted to be closed toward one another to secure the holder about the wrist,
   b) tightening strands associated with said flaps,
   c) a tightener connected with all the strands to be pulled to tension the strands as the first and second flaps are moved toward one another, the tightener then being adjustably connectible to the holder to adjustably tension all of the strands,
   d) and wherein the strands extend through one of said two flaps, and are simultaneously adjustably anchored to the other of said two flaps,
   e) there being an over flap detachably and adjustably carried by said second flap, said strands anchored to said over flap, to adjustably position strand ends relative to said second flap.

15. The combination of claim 14 wherein the tightener is adjustably attached in face to face relation with the over flap whereby the over flap is sandwiched between the tightener and said second flap, in fastened condition of the brace to the wrist.

16. In a wrist brace, the combination comprising
   a) flexible flap means defining an interior space to receive a wrist,
   b) tightening strands to hold the flap means to the wrist,
   c) the strands having opposite ends including anchoring ends, and pulled ends spaced lengthwise of the strands from said anchoring ends, all of said pulled ends connected to a tightener,
   d) the positioning of said anchoring ends being bodily adjustable by the tightener relative to the flap means, and the positions of said pulled ends being bodily adjustable relative to the flap means and relative to the anchoring ends,
   e) there being an over flap to which said anchoring ends are anchored, said over flap carried by said flap means.

17. The combination of claim 16 wherein said tightener is a flap attached to said pulled ends, and having adjustable position characterized in that said over flap is sandwiched and secured between said tightener flap and said flexible flap means.

18. The combination of claim 16 including a flap extension to receive the user's thumb, there being a stiffener at and extending lengthwise of the flap means, and a stiffener extension at said flap extension.

* * * * *